United States Patent [19]
Sheehan

[11] 3,939,151
[45] Feb. 17, 1976

[54] DISPLACEMENT OF THE THIAZOLIDINE RING IN PENICILLIN WITH THE FORMATION OF A BIOLOGICALLY ACTIVE CEPHEM SYSTEM

[75] Inventor: John C. Sheehan, Lexington, Mass.

[73] Assignee: Massachusetts Institute of Technology, Cambridge, Mass.

[22] Filed: July 25, 1974

[21] Appl. No.: 491,873

[52] U.S. Cl............ 260/243 C; 424/246; 260/239.1
[51] Int. Cl.² ....................................... C07D 501/24
[58] Field of Search ............................... 260/243 C

[56] References Cited
UNITED STATES PATENTS
3,849,408  11/1974  Dolfini .......................... 260/243 C Primary Examiner—Nicholas S. Rizzo
Attorney, Agent, or Firm—Arthur A. Smith, Jr.; Robert L. Goldberg; Robert Shaw

[57] ABSTRACT

This invention relates to a new, biologically active material conforming to the formula

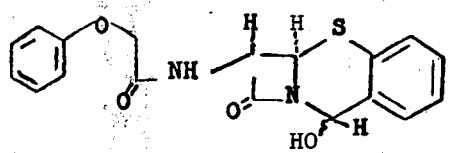

The material is formed by a process comprising displacement of the thiazolidine ring in Pencillin V and formation of the cephem system.

1 Claim, No Drawings

DISPLACEMENT OF THE THIAZOLIDINE RING IN PENICILLIN WITH THE FORMATION OF A BIOLOGICALLY ACTIVE CEPHEM SYSTEM

INTRODUCTION

This invention relates to the formation of a new biologically active material formed from Penicillin V.

DETAILED DESCRIPTION

The first step in the formation of the biologically active material of this invention is the oxidation of Penicillin V to the sulfone using a procedure as follows:

EXAMPLE 1

Penicillin V sulfone

A stirred, cold solution of 38.8g (.01 m) Pen VK+ in 600 ml water was treated by dropwise addition of a solution of 24.0g (0.14 m) of potassium permaganate and 16.4g (0.14 m) phosphoric acid in 600 ml cold water. The reaction mixture was kept cold and at pH 6.0–6.5 by addition of 6N potassium hydroxide. The solution was filtered and excess permanganate destroyed with sodium bisulfite. Cold ethyl acetate (1 l.) was added and the water solution acidified to pH 2 with 2N hydrochloric acid. The organic layer was dried and evaporated. The acid can be recrystallized from ethyl acetate/petroleum ether. Yield 94%; mp 149°–151°C: ir (KBr) 3450, 1800, 1735, 1675, 1600, 1530, 1325, 1240 cm$^{-1}$; nmr (acetone-d$_6$) $\delta$ 8.0 (d, 1, NH), 7.1 (m, 5, phenyl), 6.1 (dd 1, J$_1$ = 5, J$_2$ = 11 Hz, H-6), 5.1 (d, 1, J = 5Hz, H-5), 4.55 (s, 2, CH$_2$), 4.4 (s, 1, CH), 1.5, 1.3 (s, 6, CH$_3$).

The next step in the procedure involves converting the sulfone to the isocyanate and hydrolysis of same after ozide rearrangement according to the following procedure.

EXAMPLE 2

3-Phenoxyacetamide-4-(1' formyl-1'-methylethylsulfonyl)-2-azetidinone.

Penicillin V sulfone (19.1g, .05 m) in 150 ml dry tetrahydrofuran was cooled to −5°C. Pyridine (4.0 ml, .051 m) and ethyl chloroformate (5.0 ml, .05 m) were added and stirring continued at −5°C for 1 hr. Sodium azide (3.28g, .05m) in 25 ml water was added dropwise. The mixture was stirred for 15 minutes and poured into 1500 ml ice water and 25 ml benzene. The water layer was extracted with benzene; the organic layer dried (mgSO$_4$) and evaporated to 50 ml. The solution was heated to reflux with a Dean-Stark trap for 30 minutes and evaporated to give 10.8g of an oil.

This oil in 400 ml tetrahydrofuran was added dropwise to a mixture of 300 ml tetrahydrofuran, 300 ml water and 2.8 concentrated hydrochloric acid at toom temperature. The solution was extracted with methylene chloride, the organic layer extracted with water, dried (MgSO$_4$) and evaporated. The oil crystallized in benzene to give white crystals, 47%; mp 118°–119°; [$\alpha$]$^{25}$D 72.7° (c 0.5, CHCl$_3$); ir (KBr) 3400, 1805, 1675, 1600, 1530, 1315, 1245 cm$^{-1}$; nmr (CDCl$_3$) $\delta$ 8.6 (d, 1, NH), m at 7.1 (aromatic and benzene solvate), 6.05 (dd, 1, J$_1$ = 5, J$_2$ = 11 Hz, H-6), 5.3 (s, 1, H-3), 4.85 (d, 1, J = 5 Hz, H-5), 4.5 (s, 2, CH$_2$), 1.4, 1.45 (s, 6, CH$_3$). This compound seems to exist entirely in the ring-closed form since no aldehyde absorption is detectable by nmr.

The aldehyde formed above is then reduced to the corresponding alcohol as follows:

EXAMPLE 3

3-Phenoxyacetamide-4-(2'-hydroxy-1',1'-dimethylethylsulfonyl)-2-azetidinone

The product of example 2 (5.5g, 0.016 m) in 300 ml methanol was cooled to 0°C. A cold solution of potassium borohydride (0.43g, 0.0080 m) in 40 ml methanol and 40 ml water was added in one portion. The solution was stirred for 3 minutes, 6N hydrochloric acid added to pH 2, 200 ml water added and extracted three times with methylene chloride and twice with ethyl acetate. The organic layer was washed with water, dried (Mg SO$_4$) and evaporated. The oil obtained was crystallized from methylene chloride/benzene; 56% mp 142–144; [$\alpha$]$^{25}$D 28.6 (c 1, CHCl$_3$); mass spectrum (70 eV) m/e 219 [M+ - SO$_2$C-(CH$_3$)$_2$CH$_2$OH]; ir (KBr) 3300–3500, 1780, 1660, 1600, 1530, 1300, 1250 cm$^{-1}$, nmr (CDCl$_3$) $\delta$ 8.2 (d, 1, NH), 7.8 (s, 1, NH), m at 7.2 (5, phenyl), 5.95 (dd, 1, J$_1$=5, J$_2$= 10 Hz, H-6), 5.25 (d, 1, J =5 Hz, H-5), 4.55 (s, 2, CH$_2$), 3.75, 3.95 (overlapping s, 3, CH$_2$OH), 1.4, 1.3 (s, 6, CH$_3$).

The next step in the process comprises formation of an a modified azetidone in accordance with the following procedure.

EXAMPLE 4 cis and trans (1:1) 3-(phenoxyacetamido)-4-(2'-hydroxymethylphenylthio)-2-azetidinone The product of example 3 (368 mg, 1.04 mm) in methylene chloride was added dropwise to a solution of O-mercaptobenzylalcohol (163 mg, 1.2 mm) and triethylamine (101 mg, 1 mm) in 40 ml methylene dichloride. The solution was stirred for 10 minutes, washed with KHCO$_3$(5% aq.), dried (MgSO$_4$), and evaporated. The oil was crystallized from benzene/chloroform. 78%; ir (CH$_2$Cl$_2$) 3300, 1755, 1690, 1540, 1500 cm$^{-1}$; nmr (acetone-d$_6$) $\delta$ 8.7-6.9 (m, NH and aromatic 11), 5.75 (dd, ½, J$_1$ = 5, J$_2$ = 8 Hz, H-3 cis), 5.4 d, ½ J=5, H-4 cis), 5.2 (d, ½, J=2, H$_4$ trans). 4.9 (2s. 2, CH$_2$), 4.7 (2s, 2, CH$_2$), 4.4 (dd, ½, J$_1$=2, J$_2$=7 Hz, H$_3$ trans), 3.7 (s, 1, OH); mp 140°–142°; mass spectrum (70 eV) m/e 358(M+).

The desired product is then formed by oxidation with dimethyl sulfoxide and dicyclohexylcarbodiimide as follows:

EXAMPLE 5

The product of example 4, (107 mg, 0.3 mm), dicyclohexylcarbodiimide (186 mg, 0.9 mm), pyridine (23.7 mg, 0.3 mm), trifluoroacetic acid (17.1 mg, 0.15 mm) and 30 ml dimethylsulfoxide (distilled from calcium hydride) were stirred at room temperature for 16 hrs. The solution was filtered, diluted with methylene chloride and washed with water to remove DMSO, dried (MgSO$_4$) and evaporated. The residue was crystallized from acetone. 20%; mp 148°–150°; ir (CHCl$_3$) 3400, 1775, 1690, 1600, 1485 cm$^{-1}$; nmr (CDCl$_3$, cephem numbering) $\delta$ 8.0-6.9 (m, aromatic and NH), 6.0 (s, 1, H-4), 5.7 (dd, 1, J$_1$=5. J$_2$ = 8.5 Hz, H-7), 5.25 (d, 1, J = 5 Hz, H-6), 5.05 (s, 1, OH), 4.5 (s, 2, CH$_2$ ).

The product of example 5 was tested for biological activity and was shown to be active against *Diplococcus* pneumoniae, 0.4; *Streptococcus pyogenes*, 1.6; and *Staphylococcus aureus*, 6.3 (minimum inhibitory concentration in μg/ml).
I claim:
1. A biologically active material of the formula
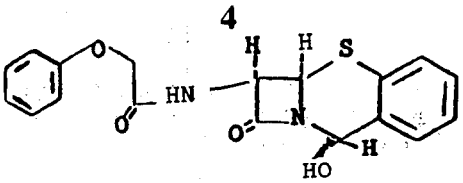
* * * * *